United States Patent
Kasuga et al.

(10) Patent No.: US 6,878,847 B2
(45) Date of Patent: Apr. 12, 2005

(54) CATALYST FOR PREPARATION OF UNSATURATED ALDEHYDE AND UNSATURATED CARBOXYLIC ACID

(75) Inventors: Hiroto Kasuga, Himeji (JP); Eiichi Shiraishi, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/827,416

(22) Filed: Apr. 20, 2004

(65) Prior Publication Data

US 2004/0199008 A1 Oct. 7, 2004

Related U.S. Application Data

(62) Division of application No. 10/100,991, filed on Mar. 20, 2002, now Pat. No. 6,784,134.

(30) Foreign Application Priority Data

Mar. 21, 2001 (JP) .......................................... 2001-80081

(51) Int. Cl.$^7$ ...................... C07C 51/16; C07C 51/235; B01J 21/18; B01J 23/40; B01J 23/00
(52) U.S. Cl. ...................... 562/532; 562/534; 562/537; 562/538; 562/546; 502/185; 502/212; 502/249; 502/255; 502/305; 502/306; 502/307; 502/308; 502/309; 502/310; 502/311; 502/313; 502/314; 502/315; 502/316; 502/317; 502/321; 502/322; 502/354; 502/407; 502/415; 502/439; 502/527.14; 502/527.24; 568/471; 568/479
(58) Field of Search ...................... 502/185, 212–249, 502/255, 305–311, 313–317, 321, 322, 354, 407, 415, 439, 527.14, 527.24; 568/471, 479; 562/532, 534, 537–538, 546

(56) References Cited

U.S. PATENT DOCUMENTS

| | | | | | |
|---|---|---|---|---|---|
| 4,558,028 A | * | 12/1985 | Tsuneki et al. | ............. | 502/211 |
| 5,602,280 A | * | 2/1997 | Nagai et al. | ................. | 562/546 |
| 5,618,974 A | * | 4/1997 | Kurimoto et al. | ........... | 562/532 |
| 5,739,392 A | * | 4/1998 | Tanimoto et al. | ........... | 562/535 |
| 5,929,275 A | * | 7/1999 | Wada et al. | ................. | 562/545 |
| 5,959,143 A | * | 9/1999 | Sugi et al. | ................... | 562/534 |
| 5,981,804 A | * | 11/1999 | Kurimoto et al. | ........... | 568/479 |
| 6,028,220 A | * | 2/2000 | Wada et al. | ................. | 562/546 |
| 6,429,332 B1 | * | 8/2002 | Tanimoto et al. | ........... | 562/532 |
| 6,476,259 B2 | * | 11/2002 | Kase et al. | ................. | 562/532 |
| 6,509,508 B2 | * | 1/2003 | Kimura et al. | ............. | 568/479 |
| 6,545,177 B2 | * | 4/2003 | Tanimoto et al. | ........... | 562/535 |
| 6,545,178 B1 | * | 4/2003 | Tanimoto et al. | ........... | 562/547 |
| 6,583,316 B1 | * | 6/2003 | Onodera et al. | ............ | 562/537 |
| 6,632,965 B1 | * | 10/2003 | Tanimoto et al. | ........... | 562/535 |
| 6,780,816 B2 | * | 8/2004 | Tanimoto et al. | ........... | 502/300 |

* cited by examiner

*Primary Examiner*—Cam N. Nguyen
(74) *Attorney, Agent, or Firm*—Sherman & Shalloway

(57) ABSTRACT

A catalyst useful for catalytic vapor-phase oxidation of isobutylene, t-butanol or propylene to produce respectively corresponding unsaturated aldehyde and unsaturated carboxylic acid is provided. The catalyst consists of ring-formed shaped bodies composed of (i) a catalyst composition containing at least molybdenum and bismuth as the active ingredients and (ii) inorganic fibers. The catalyst excels in mechanical strength, can give the object products at high yield and shows little activity degradation with time.

4 Claims, No Drawings

CATALYST FOR PREPARATION OF UNSATURATED ALDEHYDE AND UNSATURATED CARBOXYLIC ACID

CROSS REFERENCE TO RELATED APPLICATION

This application is a divisional of application Ser. No. 10/100,991, filed Mar. 20, 2002, U.S. Pat. No. 6,784,134 issued Aug. 31, 2004 which claims foreign priority to JP 2001-80081, filed Mar. 21, 2001.

TECHNICAL FIELD TO WHICH THE INVENTION BELONGS

This invention relates to catalyst for preparation of unsaturated aldehyde and unsaturated carboxylic acid. More particularly, the invention relates to a catalyst which is suitable for use in production of methacrolein and methacrylic acid, or acrolein and acrylic acid, by vapor-phase catalytic oxidation of isobutylene, tertiary butanol (which hereafter may be identified as t-butanol) or propylene. The invention also relates to processes for producing these unsaturated aldehydes and unsaturated carboxylic acids, using said catalyst.

PRIOR ART

Many proposals have been made for catalysts to be used in the occasion of vapor-phase catalytic oxidation of isobutylene, t-butanol or propylene to produce respectively corresponding unsaturated aldehyde and unsaturated carboxylic acid.

It is already known that the yield improves when the catalyst shape is changed from pellets to rings. For example, JP 59 (1984)-46132 A (=U.S. Pat. No. 4,511,671 A, EP 102,641 A1) has disclosed, as merits of adopting a specific ring form: (1) conversion improves due to increase in geometrical surface area, (2) yield improves because the reduced catalyst wall thickness enhances heat-removing effect, (3) pressure loss decreases, and (4) catalyst life is extended due to decrease in thermal load. For still increasing these effects, thinning the ring thickness is preferred. Reduction in the thickness, however, invites decrease in mechanical strength and causes such problems as, for example, when finished ring-formed catalyst is kept in a drum can, the catalyst at the bottom of the can break and become useless, or they may break when they are charged in reaction tubes and scattering in pressure loss among the reaction tubes increases.

As a method for improving strength of catalysts, it is known to add a fibrous material. For example, JP 51(1976)-20357 B relating to vanadium pentoxide catalyst, copper-chromic acid catalyst, nickel-diatomaceous earth catalyst and manganese-chromic acid catalyst, discloses a method of adding a fibrous material, for example, blue asbestos, to the catalyst powder obtained through drying or calcination and subsequent pulverization. However, effect of adding a fibrous material to catalysts comprising molybdenum and bismuth as the essential ingredients is unknown. Also as to ring-formed catalyst, addition of fibrous material gives rise to a problem of increased scattering in mechanical strength among individual catalyst rings, while their mechanical strength can be improved.

JP 59 (1984)-183832 A (=U.S. Pat. No. 4,564,607 A) discloses a method of using whiskers having an average diameter not more than 5 μm as a reinforcement, in preparation of heteropolyacid-based catalyst. Whereas, as to catalyst comprising molybdenum and bismuth as the essential ingredients, addition of whiskers results in yield reduction, while improving catalyst strength.

JP 6 (1994)-381 A (=U.S. Pat. No. 5,532,199 A, EP 574,895 A1) discloses a method of using inorganic fibers having an average diameter of 2–200 μm as assistant carrier, in preparing carried catalyst containing molybdenum and bismuth as essential ingredients. This method aims at preparation of carried catalyst in which the carrier carries a large amount of the catalyst, and for that purpose a method of preparation must be such that a slurry formed by dispersing catalytically active ingredients and inorganic fibers in a liquid is deposited on a carrier and at the same time the liquid is vaporized and evaporated. This preparation method, however, is not necessarily easy of operating, and the catalytic activity varies depending on variation in preparation conditions. Hence, there is a problem of difficulty in preparing catalyst which exhibits uniform catalytic performance.

Problems to be Solved by the Invention

Accordingly, therefore, the object of the present invention is to solve the above problems in the prior art, by providing a catalyst suitable for catalytic vapor-phase oxidation of isobutylene, t-butanol or propylene to produce corresponding unsaturated aldehyde and unsaturated carboxylic acid, i.e., a catalyst which excels in mechanical strength, is capable of providing the object products at high yield, and shows little deterioration in catalytic performance with time.

Means to Solve the Problems

Through our research work we have come to find that a catalyst for production of unsaturated aldehyde and unsaturated carboxylic acid, which is obtained by shaping a catalyst composition containing as active ingredients at least molybdenum and bismuth into rings and which additionally contains in the catalyst composition inorganic fibers such as glass fiber, alumina fiber, silica fiber, carbon fiber and the like, can accomplish the above object. The present invention is completed based on the above knowledge.

Thus, according to the invention, a catalyst for production of unsaturated aldehyde and unsaturated carboxylic acid is provided, which is characterized in that it consists of ring-shaped bodies comprising a catalytic composition containing as active ingredients at least molybdenum and bismuth, and inorganic fibers.

According to the invention, furthermore, a process is provided, which is characterized by using the above catalyst in catalytic vapor-phase oxidation of isobutylene, tertiary butanol or propylene with molecular oxygen, whereby producing respectively corresponding methacrolein and methacrylic acid or acrolein and acrylic acid.

The reason why the addition of inorganic fibers according to the present invention achieves improvements not only in the catalyst's mechanical strength but also in the catalytic performance, as well as inhibition of catalyst's deterioration with time is not fully clear yet. Presumably, because the catalyst composition is diluted with the inorganic fibers, the heat generated during the reaction is dispersed, sequential reactions are inhibited, and thermal degradation of the catalyst is inhibited. Also in view of the observation that the improvement in the catalyst's mechanical strength is achieved when the added inorganic fibers have a specific size, it is presumed that the inorganic fibers are adequately dispersed in the catalyst to maintain an adequately mixed and contacted condition with the catalyst composition.

EMBODIMENTS OF THE INVENTION

The catalyst of the present invention is of the type normally referred to as shaped catalyst, which is in the form of ring-shaped catalyst made of a catalyst composition containing molybdenum and bismuth as essential ingredients, and inorganic fibers. It is not a so called carried catalyst, formed by carrying a catalyst composition on a carrier.

As typical examples of the catalyst composition, those expressed by the following general formula (1) may be named:

$$Mo_aBi_bFe_cA_dB_eO_x \quad (1)$$

(in which Mo is molybdenum; Bi is bismuth; Fe is iron; A is at least one element selected among nickel and cobalt; B is at least an element selected among alkali metal elements, alkaline earth metal elements, thallium, phosphorus, tellurium, antimony, tin, cerium, lead, niobium, manganese, arsenic, zinc, silicon, aluminium, titanium, zirconium and tungsten; O is oxygen; a, b, c, d, e and x stand for the respective atomic numbers of Mo, Bi, Fe, A, B and O, where a is 12, b is 0.1–10, c is 0.1–20, d is 2–20; e is 0–30 and x is a numerical value determined by the extents of oxidation of the other elements).

The catalyst composition expressed by the general formula (1) can be formulated following those methods generally used for preparing this type of catalyst. As the starting materials of each of the ingredients, oxides of the ingredients or salts of the ingredients which form oxides under heating, such as nitrates, ammonium salts, organic acid salts, carbonates, alkali metal salts and the like, may be suitably selected for use.

As inorganic fibers, glass fibers, ceramic fibers, carbon fibers and the like may be used, of those, glass fibers, alumina fibers and silica fibers are preferred. In particular, glass fibers are conveniently used. More than one kind of inorganic fibers may be suitably used in combination, or those of different average fiber lengths or fiber diameters may be used in combination. Where glass fibers are used, those of different glass compositions may be suitably used in combination.

As such inorganic fibers, those having an average fiber length of 50 μm–1.5 mm, preferably 50 μm–1.2 mm, and an average fiber diameter of 2 μm–20 μm, preferably 5 μm–15 μm, are conveniently used. It is sufficient that the average fiber length falls within the above range in the completed shaped catalyst. Therefore, besides using inorganic fibers whose average length is advancedly adjusted to 50 μm–1.5 mm, it is permissible to mix inorganic fibers having an average length exceeding 1.5 mm with a part or the whole of a catalytic composition and break the fibers under vigorous agitation to eventually render their average length to fall within the range of 50 μm–1.5 mm. The latter practice, however, tends to aggravate dispersibility of the inorganic fibers. Use of inorganic fibers whose average fiber length and average fiber diameter deviate from the ranges of 50 μm–1.5 mm and 2 μm–20 μm, respectively, gives rise to problems such as that catalyst of uniform performance cannot be obtained, and therefore is objectionable.

Suitable inorganic fiber content based on the weight of the catalyst is 0.01–30%, preferably 0.05–20%, inter alia, 0.1–10%, the percentages being by weight. Where the content is too low, the effect of improving the catalyst's mechanical strength is insufficient, and where it is too high, the catalyst composition contained in the catalyst becomes less and the catalytic performance is degraded.

Those catalysts of the present invention can be prepared following those methods generally used for preparing known catalysts for production of unsaturated aldehyde and unsaturated carboxylic acid, excepting the point of adding inorganic fibers to catalyst composition and shaping the system into rings.

More specifically, a satisfactory catalyst can be prepared by adding inorganic fibers to, for example, a catalyst composition expressed by said general formula (1), and then shaping the system into rings by a conventionally used shaping method such as extrusion molding, pressing or the like. Manner of adding the inorganic fibers is not critical, and any method may be used so long as it is capable of securing uniformly dispersed presence of the added inorganic fibers in the finished catalyst. For example, inorganic fibers may be added to the starting compounds for a catalyst composition and the resulting slurry is dried and shaped, followed by calcination or a catalyst composition is dried, calcined and pulverized, and inorganic fibers are added to the resulting powder, thoroughly mixed and the mixture is shaped. In particular, the former method is favorable because it gives a catalyst exhibiting improved mechanical strength, yield of object products and catalyst life, with good reproducibility. The calcination treatment is normally conducted at temperatures ranging 400–800° C. The inorganic fibers may be added all at once or in divided portions. For example, a part of them may be added to a slurry containing starting compounds and the rest, to the dried and calcined powder.

In the occasion of shaping, conventionally used binder such as polyvinyl alcohol, stearic acid, ammonium nitrate, graphite, water, alcohol and the like may be used if necessary.

The ring-formed catalyst grains preferably each has an outer diameter of 3–10 mm, 0.1–0.7 time the outer diameter of an inner diameter and 0.5–2 times the outer diameter of a length (height).

The catalytic vapor-phase oxidation reaction according to the invention can be performed following generally practiced method for catalytic vapor-phase oxidation of isobytylene, t-butanol or propylene using molecular oxygen, to produce corresponding methacrolein and methacrylic acid, or acrolein and acrylic acid, excepting the point that above-described shaped catalyst is used as the catalyst. For example, a gaseous mixture composed of 1–10 vol. % of isobutylene, t-butanol or propylene, 3–20 vol. % of molecular oxygen, 0–60 vol. % of steam and 20–80 vol. % of an inert gas such as nitrogen, carbon dioxide and the like may be introduced over said shaped catalyst at a temperature within a range of 250–450° C., under normal pressure to 1 mpa and at a space velocity of 300–5,000 h$^{-1}$ (STP).

In practicing the catalytic vapor-phase oxidation according to the present invention, obviously such a method may be used as filling each reaction tube with two or more kinds of the catalysts differing in activity levels, which are prepared by varying the composition, calcining condition, size or shape of the catalysts, as stacked in layers so that the catalytic activity successively rises from the gas inlet toward the gas outlet of the reaction tube, to inhibit heat accumulation at hot spots, or any of various other known inhibition methods.

Effect of the Invention

According to the invention, catalysts which are high in mechanical strength, capable of giving unsaturated aldehyde and unsaturated carboxylic acid, which are the object products, at high yields, and have uniform catalytic performance showing little decrease in catalytic activity (yield reduction) with time can be prepared with ease. According to the present invention, furthermore, acrolein and acrylic acid or methacrolein and methacrylic acid can be produced at high yields over long periods.

EXAMPLES

Hereinafter the invention is explained more specifically, referring to working examples. The conversions and yields as given in the Examples and Comparative Examples are defined as follows:

$$\text{conversion (mol \%)} = \frac{\text{(mol number of reacted starting material)}}{\text{(mol number of starting material)}} \times 100$$

$$\text{yield (mol \%)} = \frac{\text{(total mol number of formed unsaturated aldehyde and formed unsaturated carboxylic acid)}}{\text{(mol number of starting material)}} \times 100$$

The performance tests and shatter strength test of the catalysts were conducted by the following methods.

Catalytic Performance Test-1

One-hundred (100) ml of a catalyst was filled in a steel reaction tube of 25 mm in inner diameter, into which a gaseous mixture composed of 6 vol. % of isobutylene, 13 vol. % of oxygen, 15 vol. % of steam and 66 vol. % of nitrogen was introduced. The reaction was conducted at a space velocity of 1600 h$^{-1}$ and a reaction temperature of 340° C. The reaction gas after 30 hours was analyzed.

Catalytic Performance Test-2

Fifteen-hundred (1,500) ml of a catalyst was filled in a steel reaction tube of 25 mm in inner diameter, and into which a gaseous mixture composed of 6 vol. % of isobutylene, 13 vol. % of oxygen, 15 vol. % of steam and 66 vol. % of nitrogen was introduced. The reaction was conducted at a space velocity of 1600 h$^{-1}$ and a reaction temperature of 340° C. The reaction gas after 8,000 hours was analyzed.

Catalytic Performance Test-3

One-hundred (100) ml of a catalyst was filled in a steel reaction tube of 25 mm in inner diameter, and into which a gaseous mixture composed of 7 vol. % of propylene, 14 vol. % of oxygen, 25 vol. % of steam and 54 vol. % of nitrogen. The reaction was conducted at a space velocity of 1800 h$^{-1}$ and a reaction temperature of 310° C. The reaction gas after 30 hours was analyzed.

Shatter Strength Test

Thirty (30) g of a catalyst was dropped from the top of a perpendicularly erected stainless steel pipe of 25 mm in inner diameter and 5 m in length, and received with a 4-mesh sieve. The weight of the catalyst remained on the sieve was measured and the shatter strength of the catalyst was determined, applying the following equation:

$$\text{Shatter strength(\%)} = \frac{\text{(weight of catalyst remained on the sieve)}}{\text{(weight of dropped catalyst)}} \times 100$$

Example 1

Six-thousand (6,000) ml of water was heated to 40° C., and into which 2118 g of ammonium paramolybdate and 530 g of ammonium paratungstate were dissolved under stirring. Thus a solution (liquid A) was prepared. Separately, 486 g of bismuth nitrate was dissolved in aqueous nitric acid solution composed of 60 ml of nitric acid (concentration: 65 wt %) and 240 ml of water to prepare another solution (liquid B). Again separately, 2912 g of cobalt nitrate and 404 g of ferric nitrate were dissolved in 2000 ml of water to form a solution (liquid C), and 78.0 g of cesium nitrate was dissolved in 400 ml of water to form a solution (liquid D). Then into the liquid A under heating and stirring, the liquid B, liquid C and liquid D were added dropwise by the order stated, and mixed. Further 406 g of 20 wt % silica sol and 68.9 g of alkali-free glass fibers of 10 μm in average fiber diameter and 500 μm in average fiber length were added to the mixture, followed by thorough stirring.

Thus obtained suspension was heated under stirring to evaporate the system to dryness, and the resulting solid matter was shaped into rings of 6.0 mm in outer diameter, 1.0 mm in inner diameter and 6.6 mm in length each, which were calcined at 500° C. for 6 hours while passing air, to provide a catalyst.

The composition of this catalyst excluding the glass fibers and oxygen was:

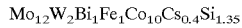

$Mo_{12}W_2Bi_1Fe_1Co_{10}Cs_{0.4}Si_{1.35}$ and its glass fiber content was 2.0 wt %.

The catalytic performance test-1 and shatter strength test were conducted using this catalyst. The catalytic performance, pressure loss during the reaction time and shatter strength of this catalyst are shown in Table 1.

Examples 2–9 and Comparative Examples 1–4

Example 1 was repeated except that the used glass fibers or shape of the catalyst were changed as shown in Table 1, to prepare catalysts.

The catalytic performance test-1 and shatter strength test were conducted using these catalysts. Their catalytic performance, pressure loss during the reaction time and shatter strength are shown in Table 1.

TABLE 1

| | Inorganic Fibers | Added amount of inorganic fibers (wt %) | Catalyst shape outer diameter × inner diameter × length (mm) | Isobutylene conversion (mol %) | Total yield of methacrolein + methafcrylic acid (mol %) | Shatter strength (%) | Pressure loss during reaction time (kPa) |
|---|---|---|---|---|---|---|---|
| Example 1 | Glass fibers (10 μmØ/500 μm-long) | 2.0 | 6.0 × 1.0 × 6.6 | 99.1 | 89.1 | 98.5 | 16.4 |
| Example 2 | Glass fibers (7 μmØ/500 μm-long) | 2.0 | 6.0 × 1.0 × 6.6 | 98.9 | 89.0 | 98.1 | 16.2 |
| Example 3 | Glass fibers (13 μmØ/500 μm-long) | 2.0 | 6.0 × 1.0 × 6.6 | 99.0 | 89.2 | 97.9 | 16.7 |
| Example 4 | Glass fibers (10 μmØ/150 μm-long) | 2.0 | 6.0 × 1.0 × 6.6 | 98.8 | 89.1 | 98.8 | 16.5 |
| Example 5 | Glass fibers (10 μmØ/3 mm-long) | 2.0 | 6.0 × 1.0 × 6.6 | 98.9 | 88.8 | 94.9 | 17.2 |
| Example 6 | Glass fibers (10 μmØ/500 μm-long) | 0.5 | 6.0 × 1.0 × 6.6 | 99.0 | 88.7 | 95.5 | 17.3 |
| Example 7 | Glass fibers (10 μmØ/500 μm-long) | 7.0 | 6.0 × 1.0 × 6.6 | 99.2 | 89.0 | 99.1 | 16.4 |
| Example 8 | Glass fiber mixture (10 μmØ/500 μm-long & 10 μmØ/3 mm-long)) | 2.0 2.0 | 6.0 × 1.0 × 6.6 | 98.9 | 89.6 | 99.0 | 16.8 |

TABLE 1-continued

|  | Inorganic Fibers | Added amount of inorganic fibers (wt %) | Catalyst shape outer diameter × inner diameter × length (mm) | Isobutylene conversion (mol %) | Total yield of methacrolein + methafcrylic acid (mol %) | Shatter strength (%) | Pressure loss during reaction time (kPa) |
|---|---|---|---|---|---|---|---|
| Example 9 | Glass fibers (10 μmØ/500 μm-long) | 2.0 | 5.0 × 3.0 × 5.5 | 99.2 | 90.2 | 95.4 | 13.1 |
| Comparative Example 1 | — | — | 6.0 × 1.0 × 6.6 | 99.0 | 88.2 | 90.4 | 18.1 |
| Comparative Example 2 | glass powder (40 μmØ) | 2.0 | 6.0 × 1.0 × 6.6 | 99.1 | 88.4 | 89.7 | 18.0 |
| Comparative Example 3 | silicon carbide (0.4 μmØ/40 μm-long) | 2.0 | 6.0 × 1.0 × 6.6 | 99.0 | 88.3 | 99.1 | 15.4 |
| Comparative Example 4 | — | — | 5.0 × 3.0 × 5.5 | 98.9 | 89.0 | 75.0 | 18.2 |

Example 10

The catalytic performance test-2 was conducted using the catalyst of Example 1. The results were: isobutylene conversion, 90.2 mol % and total yield of methacrolein plus methacrylic acid, 82.3 mol %.

Comparative Example 5

The catalytic performance test-2 was conducted using the catalyst of Comparative Example 1. The isobutylene conversion was 85.1 mol % and the total yield of methacrolein plus methacrylic acid was 76.6 mol %.

Example 11

Into 6,000 ml of water heated to 40° C., 2000 g of ammonium paramolybdate and 50 g of ammonium paratungstate were dissolved under stirring to form a solution (liquid A). Separately, 778 g of bismuth nitrate was dissolved in an aqueous nitric acid solution formed of 100 ml of nitric acid (concentration: 61 wt %) and 400 ml of water to provide a solution (liquid B). Again separately 1100 g of cobalt nitrate, 824 g of nickel nitrate and 572 g of ferric nitrate were dissolved in 2000 ml of water to form a solution (liquid C), and 7.6 g of potassium nitrate was dissolved in 100 ml of water to provide a solution (liquid D). Then into the liquid A under heating and stirring, the liquids B, C and D were added by the order stated under continual stirring and mixing, and further 242 g of 20 wt % silica sol and 151 g of alkali-free glass fibers of 10 μm in average fiber diameter and 500 μm in average fiber length were added, followed by thorough stirring.

Thus obtained suspension was heated and stirred to be evaporated to dryness, and shaped into rings of 6.0 mm in outer diameter, 1.0 mm in inner diameter and 6.6 mm in length each, which were calcined at 480° C. for 8 hours while passing air, to provide a catalyst.

The composition of this catalyst excluding the glass fibers and oxygen was:

$Mo_{12}W_{0.2}Bi_{1.7}Fe_{1.5}Co_4Ni_3K_{0.08}Si_1$ and its glass fiber content was 5 wt %.

The catalytic performance test-3 and shatter strength test were conducted using this catalyst to give a propylene conversion of 98.3 mol %, total yield of acrolein plus acrylic acid of 91.8 mol %, a pressure loss during the reaction time of 18.9 kPa and a shatter strength of 98.9%.

Comparative Example 6

Example 11 was repeated except that no glass fiber was used, to provide a catalyst.

The catalytic performance test-3 and shatter strength test were conducted using this catalyst. The propylene conversion was 98.5 mol %, total yield of acrolein plus acrylic acid was 90.9 mol %, pressure loss during the reaction time was 21.6 kPa and the shatter strength was 94.1%.

In the following Example 12 and Comparative Example 7, two kinds of catalysts exhibiting different activity levels were stacked and filled in the reaction tube in such a manner that the catalyst of the lower activity was located at the inlet side of the reaction tube and that of the higher activity, at the outlet side of the reaction tube, and the reaction was conducted.

Example 12

[Preparation of Catalyst 1 to be Stacked]

Catalyst 1 for stacking was prepared as in Example 1, except that the amount of cesium nitrate was changed to 136.4 g and the rings were shaped to have an outer diameter of 5.0 mm, an inner diameter of 3.0 mm and a length of 5.5 mm each.

The composition of this catalyst excluding the glass fibers and oxygen was:

$Mo_{12}W_2Bi_1Fe_1Co_{10}Cs_{0.7}Si_{1.35}$ and its glass fiber content was 2.0 wt %.

The results of conducting the catalytic performance test-1 and shatter strength test using this catalyst are shown in Table 2.

[Preparation of Catalyst 2 to be Stacked]

The procedures for preparing above Catalyst 1 were repeated except that the amount of cesium nitrate was changed to 19.5 g, to prepare Catalyst 2 to be stacked.

The composition of this catalyst excluding the glass fibers and oxygen was:

$Mo_{12}W_2Bi_1Fe_1Co_{10}Cs_{0.1}Si_{1.35}$ and the glass fiber content was 2.0 wt %.

The results of conducting the catalytic performance test-1 and shatter strength test are shown in Table 2.

[Reaction]

The reaction was conducted under the same conditions to those of the catalytic performance test-2, through the reaction tube filled with 750 ml of the Catalyst 1 at the gas inlet side and 750 ml of the Catalyst 2 at the gas outlet side, forming a stack. The catalytic performance after 30 hours of the reaction is shown in Table 2.

Comparative Example 7

[Preparation of Catalyst 3 to be Stacked]

Catalyst 3 was prepared in the same manner as the Catalyst 1 in Example 12, except that no glass fiber was added.

The results of conducting the catalytic performance test-1 and shatter strength test using this catalyst are shown in Table 2.

[Preparation of Catalyst 4 to be Stacked]

Catalyst 4 was prepared in the same manner as the Catalyst 2 in Example 12, except that no glass fiber was added.

The results of conducting the catalytic performance test-1 and shatter strength test using this catalyst are shown in Table 2.

[Reaction]

Filling 750 ml of said Catalyst 3 at the gas inlet side of the reaction tube and 750 ml of said Catalyst 4 at the gas outlet side thereof in a stack, the reaction was performed under the same conditions to those of the catalytic performance test-2. The catalytic performance after 30 hours of the reaction is shown in Table 2.

TABLE 2

| | | Catalyst composition | Inorganic Fibers | Added amount of Inorganic fibers (wt %) | Catalyst shape outer diameter × inner diameter × length (mm) |
|---|---|---|---|---|---|
| Example 12 | Catalyst 1 | $Mo_{12}W_2Bi_1Fe_1Co_{10}Cs_{0.7}Si_{1.35}$ | Glass fibers (10 μmØ/500 μm-long) | 2.0 | 5.0 × 3.0 × 5.5 |
| | Catalyst 2 | $Mo_{12}W_2Bi_1Fe_1Co_{10}Cs_{0.1}Si_{1.35}$ | Glass fibers (10 μmØ/500 μm-long) | 2.0 | 5.0 × 3.0 × 5.5 |
| | Reaction | Catalyst 1: 750 ml Catalyst 2: 750 ml | | | |
| Comparative Example 7 | Catalyst 3 | $Mo_{12}W_2Bi_1Fe_1Co_{10}Cs_{0.7}Si_{1.35}$ | — | — | 5.0 × 3.0 × 5.5 |
| | Catalyst 4 | $Mo_{12}W_2Bi_1Fe_1Co_{10}Cs_{0.1}Si_{1.35}$ | — | — | 5.0 × 3.0 × 5.5 |
| | Reaction | Catalyst 3: 750 ml Catalyst 4: 750 ml | | | |

| | | Isobutylene conversion (mol %) | Total yield of methacrolein + methacrylic acid (mol %) | Shatter strength (%) | Pressure loss during reaction time (kPa) |
|---|---|---|---|---|---|
| Example 12 | Catalyst 1 | 96.0 | 88.3 | 98.4 | 13.2 |
| | Catalyst 2 | 99.5 | 88.1 | 98.0 | 13.0 |
| | Reaction | 99.5 | 91.8 | — | 12.9 |
| Comparative Example 7 | Catalyst 3 | 97.1 | 86.9 | 76.4 | 17.9 |
| | Catalyst 4 | 99.8 | 86.4 | 74.3 | 18.4 |
| | Reaction | 99.7 | 90.2 | — | 18.5 |

What is claimed is:

1. A process for catalytic vapor phase oxidation of isobutylene, tertiary butanol or propylene with molecular oxygen to produce, respectively, corresponding methacrolein and methacrylic acid or acrolein and acrylic acid, the process comprises using a catalyst which is in the form of ring-shaped bodies composed of a catalyst composition containing at least molybdenum and bismuth as the active ingredients and inorganic fibers, wherein the inorganic fibers are at least one selected from the group consisting of glass fibers, alumina fibers, silica fibers and carbon fibers, and have an average fiber length of from 50 um to 1.5 mm and an average fiber diameter of from 2 um to 20 um.

2. The process of claim 1, wherein the catalyst contains from 0.01 to 30% by weight, based on the weight of the catalyst, of inorganic fibers.

3. The process of claim 2, wherein the ring-shaped bodies have an outer diameter of 3–10 mm, an inner diameter that is 0.1–0.7 times the outer diameter, and a length that is 0.5–2 times the outer diameter.

4. The process of claim 3, wherein the catalyst composition is expressed by the general formula $$MO_aBi_bFe_cA_dB_eO_x$$

wherein Mo is molybdenum; Bi is bismuth; Fe is iron; A is at least one element selected from the group consisting of nickel and cobalt; B is at least one element selected from the group consisting of alkali metal elements, alkaline earth metal elements, thallium, phosphorus, tellurium, antimony, tin, cerium, lead, niobium, manganese, arsenic, zinc, silicon, aluminum, titanium, zirconium, and tungsten; O is oxygen; a, b, c, d, e and x stand for the respective atomic numbers of Mo, Bi, Fe, A, B and O, where a is 12, b is 0.1–10, c is 0.1–20, d is 2–20, e is 0–30 and x is a numerical value determined by the extent of oxidation of the other elements.

* * * * *